United States Patent
Gao et al.

(10) Patent No.: US 8,221,978 B2
(45) Date of Patent: Jul. 17, 2012

(54) NORMALIZATION PROBES FOR COMPARATIVE GENOME HYBRIDIZATION ARRAYS

(75) Inventors: Jing Gao, San Jose, CA (US); B. Shane Giles, Fremont, CA (US); Peter G. Webb, Menlo Park, CA (US); Douglas N. Roberts, Campbell, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 441 days.

(21) Appl. No.: 12/279,570

(22) PCT Filed: Jan. 26, 2007

(86) PCT No.: PCT/US2007/002127
§ 371 (c)(1),
(2), (4) Date: Jul. 1, 2009

(87) PCT Pub. No.: WO2007/097876
PCT Pub. Date: Aug. 30, 2007

(65) Prior Publication Data
US 2009/0275482 A1  Nov. 5, 2009

(51) Int. Cl.
*C12Q 1/68* (2006.01)
*C12M 1/34* (2006.01)
*G01N 33/48* (2006.01)
*C12N 15/11* (2006.01)
*C07H 21/04* (2006.01)

(52) U.S. Cl. ................. 435/6.11; 435/287.1; 435/287.2; 536/24.3; 702/19; 702/20

(58) Field of Classification Search ...................... None
See application file for complete search history.

(56) References Cited

U.S. PATENT DOCUMENTS

| 6,548,257 B2 * | 4/2003 | Lockhart et al. ................. 506/9 |
| 2004/0219565 A1 | 11/2004 | Kauppinen et al. |
| 2005/0079509 A1 | 4/2005 | Shannon |
| 2006/0110744 A1 | 5/2006 | Sampas et al. |

OTHER PUBLICATIONS

Skvortsov, Dmitriy et al., Using expression arrays for copy number detection: an example from *E. coli*, BMC Bioinformatics, 2007, p. 203-225, vol. 8.
International Search Report and Written Opinion of the International Searching Authority, mailed Feb. 4, 2008 in PCT/US2007/002127, filed Jan. 26, 2007, 11 pages.

* cited by examiner

*Primary Examiner* — James Martinell

(57) ABSTRACT

A method of selecting a set of normalization probes for use on a comparative genome hybridization array is provided. In certain embodiments, the method includes: a) selecting a first region of a genome to be evaluated by comparative genome hybridization to produce data; b) selecting a second region of the genome for normalization of the data, and c) selecting from a set of candidate probes a sub-set of normalization probes that detect the second region.

26 Claims, 2 Drawing Sheets

NORMALIZATION PROBES FOR COMPARATIVE GENOME HYBRIDIZATION ARRAYS

BACKGROUND

Comparative genomic hybridization (CGH) is one approach that has been employed to detect the presence and identify the location of amplified or deleted sequences in a genome. In one implementation of CGH, genomic DNA is isolated from normal reference cells, as well as from test cells. The two genomic DNAs are differentially labeled and then simultaneously hybridized to an array of surface-bound polynucleotide probes, e.g., an array of BACs, cDNAs or oligonucleotides. Chromosomal regions in the test cells which are at increased or decreased copy number can be identified by detecting regions where the ratio of signal from the two distinguishably labeled nucleic acids is altered. For example, those regions that have been decreased in copy number in the test cells will show relatively lower signal from the test nucleic acid than the reference compared to other regions of the genome. Regions that have been increased in copy number in the test cells will show relatively higher signal from the test nucleic acid.

SUMMARY

A method of selecting a set of normalization probes for use on a comparative genome hybridization array is provided. In certain embodiments, the method includes: a) selecting a first region of a genome to be evaluated by comparative genome hybridization to produce data; b) selecting a second region of the genome for normalization of the data, and c) selecting from a set of candidate probes a sub-set of normalization probes that detect the second region.

DEFINITIONS

Figure 1:
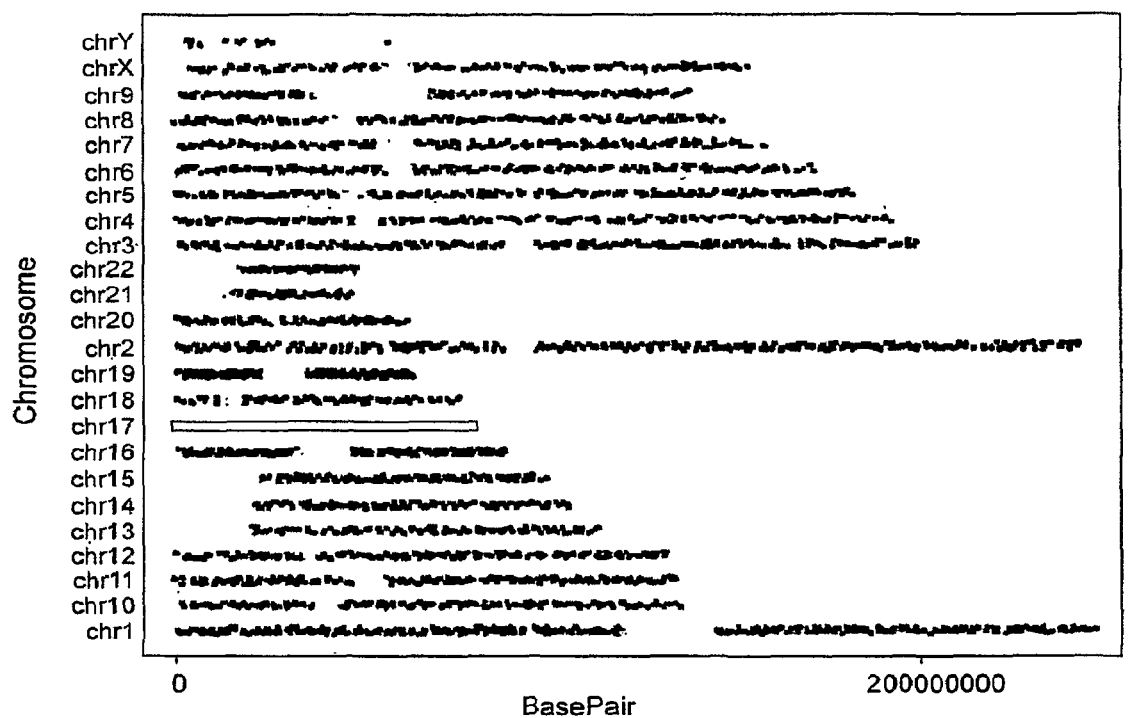
FIG. 1 schematically illustrates the positioning of 3714 exemplary normalization probes used for normalizing data for chromosome 17. Normalization probes are shown as filled squares, whereas chromosome 17 is shown as an unfilled rectangle.

A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. As such, this term includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes deoxyribonucleic acid or DNA (including cDNA), ribonucleic acid or RNA and oligonucleotides, regardless of the source.

The terms "ribonucleic acid" and "RNA" as used herein mean a polymer composed of ribonucleosides.

The terms "deoxyribonucleic acid" and "DNA" as used herein mean a polymer composed of deoxyribonucleotides.

The term "mRNA" means messenger RNA.

A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Nucleotide sub-units of deoxyribonucleic acids are deoxyribonucleotides, and nucleotide sub-units of ribonucleic acids are ribonucleotides.

An "oligonucleotide" generally refers to a nucleotide multimer of about 2 to about 200 nucleotides in length (e.g., about 10 to about 100 nucleotides or about 30 to about 80 nucleotides) while a "polynucleotide" or "nucleic acid" includes a nucleotide multimer having any number of nucleotides. Oligonucleotides may be synthetic A chemical "array", unless a contrary intention appears, includes any one, two or three-dimensional arrangement of addressable regions bearing a particular chemical moiety or moieties (for example, biopolymers such as polynucleotide sequences) associated with that region, where the chemical moiety or moieties are immobilized on the surface in that region. By "immobilized" is meant that the moiety or moieties are stably associated with the substrate surface in the region, such that they do not separate from the region under conditions of using the array, e.g., hybridization and washing and stripping conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. An array may contain more than ten, more than one hundred, more than one thousand more than ten thousand features, or even more than one hundred thousand features, in an area of less than 20 cm$^2$ or even less than 10 cm$^2$. For example, features may have widths (that is, diameter, for a round spot) in the range of from about 10 μm to about 1.0 cm. In other embodiments each feature may have a width in the range of about 1.0 μm to about 1.0 mm, such as from about 5.0 μm to about 500 μm, and including from about 10 μm to about 200 μm. Non-round features may have area ranges equivalent to that of circular features with the foregoing width (diameter) ranges. A given feature is made up of chemical moieties, e.g., nucleic acids, that bind to (e.g., hybridize to) the same target (e.g., target nucleic acid), such that a given feature corresponds to a particular target. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide. Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations. An array is "addressable" in that it has multiple regions (sometimes referenced as "features" or "spots" of the array) of different moieties (for example, different polynucleotide sequences) such that a region at a particular predetermined location (an "address") on the array will detect a particular target or class of targets (although a feature may incidentally detect non-targets of that feature). The target for which each feature is specific is, in representative embodiments, known. An array feature is generally homogenous in composition and concentration and the features may be separated by intervening spaces (although arrays without such separation can be fabricated).

The term "substrate" as used herein refers to a surface upon which probes, e.g., an array, may be adhered. Substrates may be porous or non-porous, planar or non-planar over all or a portion of their surface. Glass slides are the most common substrate for arrays, although fused silica, silicon, plastic and other materials are also suitable. A substrate may contain more than one array.

The phrase "oligonucleotide bound to a surface of a solid support" or "probe bound to a solid support" or a "target bound to a solid support" refers to an oligonucleotide or mimetic thereof, e.g., PNA, LNA or UNA molecule that is immobilized on a surface of a solid substrate, where the substrate can have a variety of configurations, e.g., a sheet, bead, particle, slide, wafer, web, fiber, tube, capillary, microfluidic channel or reservoir, or other structure. The support can be planar, nonplanar or a combination thereof. The support can be porous or non-porous. In certain embodiments, the collections of oligonucleotide elements employed herein are present on a surface of the same planar support, e.g., in the form of an array. It should be understood that the terms "probe" and "target" are relative terms and that a molecule considered as a probe in certain assays may function as a target in other assays.

"Addressable sets of probes" and analogous terms refer to the multiple known regions of different moieties of known characteristics (e.g., base sequence composition) supported by or intended to be supported by an array surface, such that each location is associated with a moiety of a known characteristic and such that properties of a target moiety can be determined based on the location on the array surface to which the target moiety binds under stringent conditions.

In certain embodiments, an array is contacted with a nucleic acid sample under stringent assay conditions, i.e., conditions that are compatible with producing bound pairs of biopolymers of sufficient affinity to provide for the desired level of specificity in the assay while being less compatible to the formation of binding pairs between binding members of insufficient affinity. Stringent assay conditions are the summation or combination (totality) of both binding conditions and wash conditions for removing unbound molecules from the array.

As known in the art, "stringent hybridization conditions" and "stringent hybridization wash conditions" in the context of nucleic acid hybridization are sequence dependent, and are different under different experimental parameters. Stringent hybridization conditions include, but are not limited to, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization in 0.5 M NaHPO4, 7% sodium dodecyl sulfate (SDS), 1 mM EDTA at 65° C., and washing in 0.1×SSC/0.1% SDS at 68° C. can be performed. Additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

Wash conditions used to remove unbound nucleic acids may include, e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature. Other methods of agitation can be used, e.g., shaking, spinning, and the like.

Stringent hybridization conditions may also include a "pre-hybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate. The term "highly stringent hybridization conditions" as used herein refers to conditions that are compatible to produce complexes between complementary binding members, i.e., between immobilized probes and complementary sample nucleic acids, but which does not result in any substantial complex formation between non-complementary nucleic acids (e.g., any complex formation which cannot be detected by normalizing against background signals to interfeature areas and/or control regions on the array).

Additional hybridization methods are described in references describing CGH techniques (Kallioniemi et al., *Science* 1992; 258:818-821 and WO 93/18186). Several guides to general techniques are available, e.g., Tijssen, *Hybridization*

*with Nucleic Acid Probes*, Parts I and II (Elsevier, Amsterdam 1993). For a descriptions of techniques suitable for in situ hybridizations see, Gall et al. *Meth. Enzymol.* 1981; 21:470-480 and Angerer et al., In *Genetic Engineering Principles and Methods*, Setlow and Hollaender, Eds. Vol 7, pgs 43-65 (Plenum Press, New York 1985). See also U.S. Pat. Nos. 6,335, 167; 6,197,501; 5,830,645; and 5,665,549; the disclosures of which are herein incorporated by reference.

The term "sample" as used herein relates to a material or mixture of materials, containing one or more components of interest. Samples include, but are not limited to, samples obtained from an organism or from the environment (e.g., a soil sample, water sample, etc.) and may be directly obtained from a source (e.g., such as a biopsy or from a tumor) or indirectly obtained e.g., after culturing and/or one or more processing steps. In one embodiment, samples are a complex mixture of molecules, e.g., comprising about 50 or more different molecules, about 100 or more different molecules, about 200 or more different molecules, about 500 or more different molecules, about 1000 or more different molecules, about 5000 or more different molecules, about 10,000 or more molecules, etc.

The term "genome" refers to all nucleic acid sequences (coding and non-coding) and elements present in any virus, single cell (prokaryote and eukaryote) or each cell type in a metazoan organism. The term genome also applies to any naturally occurring or induced variation of these sequences that may be present in a mutant or disease variant of any virus or cell or cell type. Genomic sequences include, but are not limited to, those involved in the maintenance, replication, segregation, and generation of higher order structures (e.g. folding and compaction of DNA in chromatin and chromosomes), or other functions, if any, of nucleic acids, as well as all the coding regions and their corresponding regulatory elements needed to produce and maintain each virus, cell or cell type in a given organism.

For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence.

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

As used herein, a "test nucleic acid sample" or "test nucleic acids" refer to nucleic acids comprising sequences whose quantity or degree of representation (e.g., copy number) or sequence identity is being assayed. Similarly, "test genomic acids" or a "test genomic sample" refers to genomic nucleic acids comprising sequences whose quantity or degree of representation (e.g., copy number) or sequence identity is being assayed.

Similarly, "reference genomic acids" or a "reference genomic sample" refers to genomic nucleic acids comprising sequences whose quantity or degree of representation (e.g., copy number) or sequence identity is to be compared with a test nucleic acids. A "reference nucleic acid sample" may be derived independently from a "test nucleic acid sample," i.e., the samples can be obtained from different organisms or different cell populations of the sample organism. However, in certain embodiments, a reference nucleic acid is present in a "test nucleic acid sample" which comprises one or more sequences whose quantity or identity or degree of representation in the sample is unknown while containing one or more sequences (the reference sequences) whose quantity or identity or degree of representation in the sample is known. The reference nucleic acid may be naturally present in a sample (e.g., present in the cell from which the sample was obtained) or may be added to or spiked in the sample.

If a surface-bound polynucleotide or probe "corresponds to" a chromosome, the polynucleotide usually contains a sequence of nucleic acids that is unique to that chromosome. Accordingly, a surface-bound polynucleotide that corresponds to a particular chromosome usually specifically hybridizes to a labeled nucleic acid made from that chromosome, relative to labeled nucleic acids made from other chromosomes. Array features, because they usually contain surface-bound polynucleotides, can also correspond to a chromosome.

A "CGH array" or "aCGH array" refers to an array that can be used to compare DNA samples for relative differences in copy number. In general, an aCGH array can be used in any assay in which it is desirable to scan a genome with a sample of nucleic acids. For example, an aCGH array can be used in location analysis as described in U.S. Pat. No. 6,410,243, the entirety of which is incorporated herein and thus can also be referred to as a "location analysis array" or an "array for ChIP-chip analysis." In certain aspects, a CGH array provides probes for screening or scanning a genome of an organism and comprises probes from a plurality of regions of the genome.

In one aspect, the array comprises probe sequences for scanning an entire chromosome arm, wherein probes targets are separated by about 500 bp or more, about 1 kb or more, about 5 kb or more, about 10 kb or more, about 25 kb or more, about 50 kb or more, about 100 kb or more, about 250 kb or more, about 500 kb or more and about 1 Mb or more. In another aspect, the array comprises probes sequences for scanning an entire chromosome, a set of chromosomes, or the complete complement of chromosomes forming the organism's genome. By "resolution" is meant the spacing on the genome between sequences found in the probes on the array. In some embodiments (e.g., using a large number of probes of high complexity) all sequences in the genome can be present in the array. The spacing between different locations of the genome that are represented in the probes may also vary, and may be uniform, such that the spacing is substantially the same between sampled regions, or non-uniform, as desired. An assay performed at low resolution on one array, e.g., comprising probe targets separated by larger distances, may be repeated at higher resolution on another array, e.g., comprising probe targets separated by smaller distances.

In certain aspects, in constructing arrays, both coding and non-coding genomic regions are included as probes, whereby "coding region" refers to a region comprising one or more exons that is transcribed into an mRNA product and from there translated into a protein product, while by non-coding region is meant any sequences outside of the exon regions, where such regions may include regulatory sequences, e.g., promoters, enhancers, untranslated but transcribed regions, introns, origins of replication, telomeres, etc. In certain embodiments, one can have at least some of the probes directed to non-coding regions and others directed to coding regions. In certain embodiments, one can have all of the probes directed to non-coding sequences and such sequences can, optionally, be all non-transcribed sequences (e.g., intergenic regions including regulatory sequences such as promoters and/or enhancers lying outside of transcribed regions).

In certain aspects, an array may be optimized for one type of genome scanning application compared to another, for example, the array can be enriched for intergenic regions compared to coding regions for a location analysis application.

In some embodiments, at least 5% of the polynucleotide probes on the solid support hybridize to regulatory regions of a nucleotide sample of interest while other embodiments may have at least 30% of the polynucleotide probes on the solid support hybridize to exonic regions of a nucleotide sample of interest. In yet other embodiments, at least 50% of the polynucleotide probes on the solid support hybridize to intergenic regions (e.g., non-coding regions which exclude introns and untranslated regions, i.e, comprise non-transcribed sequences) of a nucleotide sample of interest.

In certain aspects, probes on the array represent random selection of genomic sequences (e.g., both coding and non-coding). However, in other aspects, particular regions of the genome are selected for representation on the array, e.g., such as CpG islands, genes belonging to particular pathways of interest or whose expression and/or copy number are associated with particular physiological responses of interest (e.g., disease, such a cancer, drug resistance, toxological responses and the like). In certain aspects, where particular genes are identified as being of interest, intergenic regions proximal to those genes are included on the array along with, optionally, all or portions of the coding sequence corresponding to the genes. In one aspect, at least about 100 bp, 500 bp, 1,000 bp, 5,000 bp, 10,000 kb or even 100,000 kb of genomic DNA upstream of a transcriptional start site is represented on the array in discrete or overlapping sequence probes. In certain aspects, at least one probe sequence comprises a motif sequence to which a protein of interest (e.g., such as a transcription factor) is known or suspected to bind.

In certain aspects, repetitive sequences are excluded as probes on the arrays. However, in another aspect, repetitive sequences are included.

The choice of nucleic acids to use as probes may be influenced by prior knowledge of the association of a particular chromosome or chromosomal region with certain disease conditions. International Application WO 93/18186 provides a list of exemplary chromosomal abnormalities and associated diseases, which are described in the scientific literature. Alternatively, whole genome screening to identify new regions subject to frequent changes in copy number can be performed using the methods of the present invention discussed further below.

In some embodiments, previously identified regions from a particular chromosomal region of interest are used as probes. In certain embodiments, the array can include probes which "tile" a particular region (e.g., which have been identified in a previous assay or from a genetic analysis of linkage), by which is meant that the probes correspond to a region of interest as well as genomic sequences found at deemed intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled array tailored to the initially identified region to further assay the region at a higher resolution, e.g., in an iterative protocol.

In certain aspects, the array includes probes to sequences associated with diseases associated with chromosomal imbalances for prenatal testing. For example, in one aspect, the array comprises probes complementary to all or a portion of chromosome 21 (e.g., Down's syndrome), all or a portion of the X chromosome (e.g., to detect an X chromosome deficiency as in Tuner's Syndrome) and/or all or a portion of the Y chromosome Klinefelter Syndrome (to detect duplication of an X chromosome and the presence of a Y chromosome), all or a portion of chromosome 7 (e.g., to detect William's Syndrome), all or a portion of chromosome 8 (e.g., to detect Langer-Giedon Syndrome), all or a portion of chromosome 15 (e.g., to detect Prader-Willi or Angelman's Syndrome, all or a portion of chromosome 22 (e.g., to detect Di George's syndrome).

Other "themed" arrays may be fabricated, for example, arrays including whose duplications or deletions are associated with specific types of cancer (e.g., breast cancer, prostate cancer and the like). The selection of such arrays may be based on patient information such as familial inheritance of particular genetic abnormalities. In certain aspects, an array for scanning an entire genome is first contacted with a sample and then a higher-resolution array is selected based on the results of such scanning. Themed arrays also can be fabricated for use in gene expression assays, for example, to detect expression of genes involved in selected pathways of interest, or genes associated with particular diseases of interest.

In one embodiment, a plurality of probes on the array are selected to have a duplex $T_m$ within a predetermined range. For example, in one aspect, about 50% or more of the probes have a duplex $T_m$ within a temperature range of about 75° C. to about 85° C. In one embodiment, at least 80% of said polynucleotide probes have a duplex $T_m$ within a temperature range of about 75° C. to about 85° C., within a range of about 77° C. to about 83° C., within a range of from about 78° C. to about 82° C. or within a range from about 79° C. to about 82° C. In one aspect, about 50% or more of the probes on an array have range of $T_m$'s of less than about 4° C., less than about 3° C., or even less than about 2° C., e.g., less than about 1.5° C., less than about 1.0° C. or about 0.5° C.

In certain embodiments, the probes on the microarray have a nucleotide length in the range of at least 30 nucleotides to 200 nucleotides, or in the range of about 30 to about 150 nucleotides. In other embodiments, about 50% or more of the polynucleotide probes on the solid support have the same nucleotide length, and that length may be about 60 nucleotides.

In still other aspects, probes on the array comprise at least coding sequences.

In one aspect, probes represent sequences from an organism such as *Drosophila melanogaster, Caenorhabditis elegans*, yeast, zebrafish, a mouse, a rat, a domestic animal, a companion animal, a primate, a human, etc. In certain aspects, probes representing sequences from different organisms are provided on a single substrate, e.g., on a plurality of different arrays.

A "CGH assay" using an aCGH array can be generally performed as follows. In one embodiment, a population of nucleic acids contacted with an aCGH array comprises at least two sets of nucleic acid populations, which can be derived from different sample sources. For example, in one aspect, a target population contacted with the array comprises a set of target molecules from a reference sample and from a test sample. In one aspect, the reference sample is from an organism having a known genotype and/or phenotype, while the test sample has an unknown genotype and/or phenotype or a genotype and/or phenotype that is known and is different from that of the reference sample. For example, in one aspect, the reference sample is from a healthy patient while the test sample is from a patient suspected of having cancer or known to have cancer.

In one embodiment, a target population being contacted to an array in a given assay comprises at least two sets of target populations that are differentially labeled (e.g., by spectrally distinguishable labels). In one aspect, control target molecules in a target population are also provided as two sets, e.g., a first set labeled with a first label and a second set labeled with a second label corresponding to first and second labels being used to label reference and test target molecules, respectively.

In one aspect, the control target molecules in a population are present at a level comparable to a haploid amount of a gene represented in the target population. In another aspect, the control target molecules are present at a level comparable to a diploid amount of a gene. In still another aspect, the control target molecules are present at a level that is different from a haploid or diploid amount of a gene represented in the target population. The relative proportions of complexes formed labeled with the first label vs. the second label can be used to evaluate relative copy numbers of targets found in the two samples.

In certain aspects, test and reference populations of nucleic acids may be applied separately to separate but identical arrays (e.g., having identical probe molecules) and the signals from each array can be compared to determine relative copy numbers of the nucleic acids in the test and reference populations.

Methods to fabricate arrays are described in detail in U.S. Pat. Nos. 6,242,266; 6,232,072; 6,180,351; 6,171,797 and 6,323,043. As already mentioned, these references are 20, incorporated herein by reference. Drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT. MICROARRAY SCANNER manufactured by Agilent Technologies, Palo, Alto, Calif. or other similar scanner. Other suitable apparatus and methods are described in U.S. Pat. Nos. 6,518, 556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques or electrical techniques (where each feature is provided with an electrode to detect bonding at that feature in a manner disclosed in U.S. Pat. Nos. 6,251,685, 6,221,583 and elsewhere).

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

By "remote location" is meant a location other than the location at which an array is present and hybridization occurs. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

"Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

DETAILED DESCRIPTION

A method of selecting a set of normalization probes for use on a comparative genome hybridization array is provided. In certain embodiments, the method includes: a) selecting a first region of a genome to be evaluated by comparative genome hybridization to produce data; b) selecting a second region of the genome for normalization of the data, and c) selecting from a set of candidate probes a sub-set of normalization probes that detect the second region.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components that are described in the publications that might be used in connection with the presently described invention.

Methods

In certain embodiments, the instant probe selection methods include selecting a first region of a genome for analysis and selecting a second region of the genome for normalizing data obtained for the first region. The second region is generally different from the first region. In certain embodiments, the second region is larger than the first region and may, in particular embodiments, encompasses the first region. In other embodiments, the second region may be distinct from (i.e., non-overlapping with) the first region. In other words, the second region is not the same as the first region. Normalization probes may then be selected for detecting the second region. The normalization probes are generally selected from a larger set of candidate probes, i.e., a set of probes containing probes that are greater in number than the normalization probe set. In one embodiment, the probes of the set of candidate probes are ranked according to a property, e.g., according to their predicted performance, and candidate probes are selected in such a way as to provide a set of normalization probes that includes not only the highest ranked probes, but also probes that are distributed evenly across the second region.

A set of probes for analysis (i.e., a set of "analysis probes") for the first region of the genome may be selected, and an array containing those analysis probes and a set of normalization probes, as discussed above, may be produced. Data produced using the analysis probes may be normalized using the results obtained from the normalization probes. The second region may be, for example, an entire genome (including or excluding the second region) or any region that may be expected to have a known copy number.

In a certain embodiments, normalization probes for the second region of a genome may be selected from a set of candidate probes using a pairwise probe selection method. These embodiments may involve iteratively analyzing neighboring candidate probe sequences within the second region, and selecting one of probes for inclusion in the normalization probe set. In certain embodiments, the candidate probes may be ranked according to one or more properties (e.g., thermodynamic or performance properties), and the probe that is selected from the neighboring probe pair may have the higher ranking.

In some embodiments, data produced by the instant methods, which may include normalized data and raw data, may be communicated to a client that may be local or remote to the position in which the hybridization reactions are performed. As noted above, data may be communicated to a client, for example, electronically via the internet or by mail, for example. In particular cases, data for candidate probes and the normalization probes may be communicated. In other cases, data for the candidate probes and not data for the normalization probes may be communicated. In such cases, the data for the candidate probes may be normalized before it is communicated.

Region for Analysis

As noted above, a first region of a genome is selected for analysis. The region selected for analysis may be any part of a genome, including, for example, a particular locus, a gene, a group of genes, or any other part of a chromosome, such as a chromosome arm or an entire chromosome. The region selected for analysis may, in certain embodiments, be known to contain or suspected of containing an area of altered copy number, e.g., a duplicated, translocated, rearranged, or deleted region, in relation to a wild-type chromosome. In other embodiments, the region selected for analysis may be arbitrarily chosen and may not be known to contain an area of altered copy number. The region selected for analysis may be anywhere in the range of about 10 kb to about the length of an entire chromosome in size. The length of the region selected for analysis may be in the range of about 10 kb to about 50 kb in size, about 50 kb to about 200 kb in size, about 200 kb to about 1 Mb in size, about 1. Mb to about 5 Mb in size, about 1 Mb to about 5 Mb in size, about 5 Mb to about 25 Mb in size, or about 25 Mb to about 150 Mb in size, for example. In certain embodiments, the region selected for analysis may be in the range of about 100 kb to about 100 Mb in size. In a particular embodiment, the region for analysis may be a region indicated as having altered copy number by cytogenetic experiments.

Region for Normalization

Figure 2:
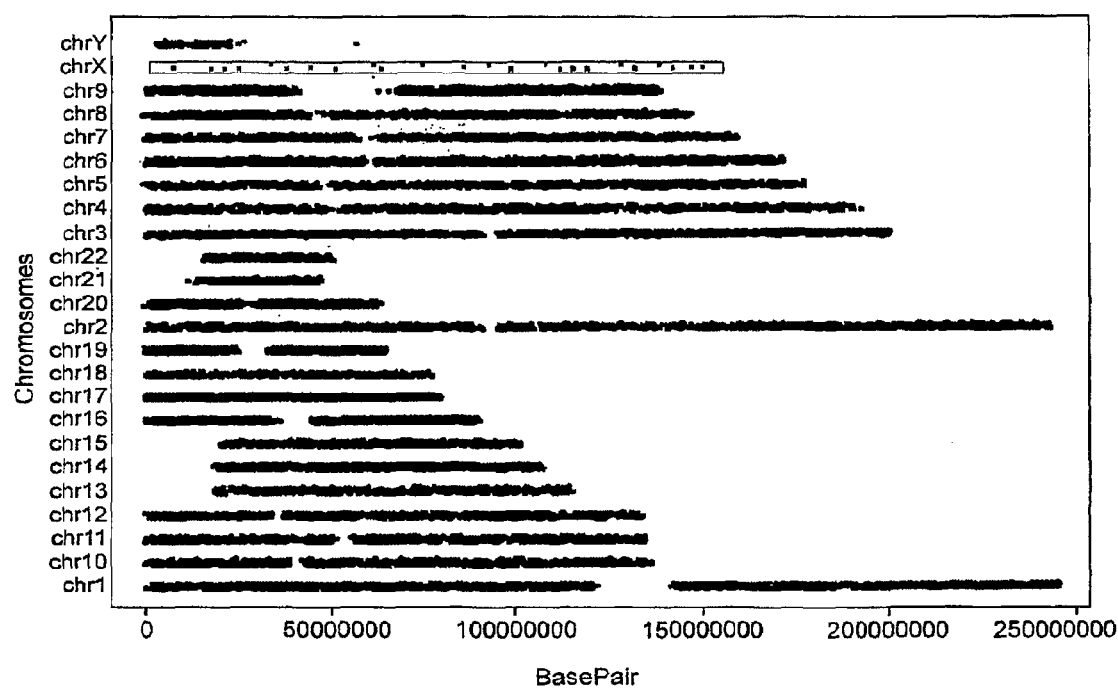
FIG. 2 schematically illustrates the positioning of 20290 exemplary normalization probes used for normalizing data for the X chromosome. Normalization probes are shown as filled squares, whereas the X chromosome is shown as an unfilled rectangle.

The region selected for normalization is different from the region selected for analysis. In certain embodiments, the region selected for normalization may be larger than the region selected for analysis and may encompass the region for selected for analysis. For example, the region selected for normalization may be the entire genome of the cell under study, including the region selected for analysis. In other embodiments, the region selected for normalization may be distinct and non-overlapping with the region selected for normalization. For example, the region selected for normalization may be: a) the entire genome of the cell under study, excluding the region selected for analysis, b) part of a different chromosome to the region selected for analysis, or c) part a different chromosome arm to the region selected for analysis. The region selected for normalization may be arbitrarily selected or, in certain embodiments, may be expected to have a known copy number. In the example shown in FIG. 1, 3714 exemplary normalization probes are selected for normalizing data for chromosome 17. In this example, none of the normalization probes are for detecting chromosome 17. In the example shown in FIG. 2, 20290 exemplary normalization probes are selected for normalizing data for the X chromosome. In this example, some of the normalization probes detect the X chromosome.

Probe Selection

Probes that detect the region for normalization (termed "normalization probes" herein) may be in certain embodiments designed or selected using known methods.

In certain embodiments, the normalization probes are selected from a pre-existing set of candidate probes. The set of candidate probes may contain about 1000 or more probes, e.g., about 5000 or more probes, about 10,000 or more probes, about 20,000 or more probes, about 30,000 or more probes or about 40,000 or more probes, up to about 50,000 probes or 100,000 or more probes, which bind to unique sequences within a genome of interest. In certain embodiments, the candidate probes of the set of candidate probes bind to positions that are distributed across the genome being examined. The candidate probes may bind to positions that are distributed across the genome that have an average interval in the range of, for example, every 50 bp to 200 bp, every 200 bp to 500 bp, every 500 bp to 1 kb, every 1 kb to 5 kb or every 5 to 20 kb, or at an interval that is greater than about 20 kb. The probes of the set of candidate probes may be designed to have similar thermodynamic properties, e.g., similar $T_m$s, G/C content, hairpin stability, etc.

In particular embodiments, at least 70% of the candidate probes in the set of candidate probes have a duplex Tm value ranging from about 65° C. to about 85° C., e.g., from about 75° C. to about 85° C., a length in the range of about 40 nucleotides to 70 nucleotides, e.g., about 50 to 65 nucleotides, and a GC content of about 30 to about 50%. Further details of an exemplary candidate probe set that may be employed herein are described in U.S. application Ser. No. 10/996,323, filed on Nov. 23, 2004, which application is incorporated by reference herein in its entirety.

In certain embodiments, the probes of the set of candidate probes may be validated probes in that they have been tested experimentally, e.g., in silico or in a hybridization experiments, and found to provide results that are compatible with future use as a normalization probe. Validated probes may be selected because they provide results that are within the range expected for a suitable normalization probe. The range of results for a suitable normalization probe may be arbitrarily defined or readily determined experimentally or computationally. Suitable normalization probes may produce suitable signal intensities in both channels, exhibit little dye bias, bind stably during washing, and produce signals that persist, for example.

In particular embodiments, the candidate probes may be ranked prior to or after selection of the normalization probes. In one embodiment, the candidate probes may be scored according one or more or a combination of properties. Such properties, which may be experimentally determined or computationally predicted, include: probe performance properties, including signal intensity when bound to a complementary target sequence, dye bias, susceptibility to non-specific binding, wash stability and persistence of probe hybridization (e.g., during an experiment and/or after stripping an array), evaluation of binding to a plurality of different target sequences (e.g., which may vary by a single base), evaluation of binding to a target gene in a complex sample, comprising, e.g., a whole genome of sequences, slope of a response curve, reproducibility or noise, P-value of separability of distributions based on repeated measurements at two or more target copy number values, variance of signals, variance of ratios, or thermodynamic properties, e.g., duplex melting temperature, hairpin stability, GC content, etc.; and other properties, such as whether a probe binds to an exon, intron, promoter, intergenic region, coding sequence or another other sequence motif. Such ranking may be done by assigning a property score, e.g., an integer, for example, to each of the candidate probes.

In one embodiment, the normalization probes may be selected from the candidate probes by a pairwise probe selection process. This pairwise probe selection process may include selecting the candidate probes that bind to region for normalization, and then out of probes that bind to the region for normalization, selecting a predetermined number of normalization probes. The pairwise probe selection process, in certain embodiments, provides for the "best" probes (i.e., those with the highest ranking), while maintaining an even distribution of those probes across the region for normalization. In one embodiment, the probe selection process is an iterative process that includes the following acts: a) pairing the most proximal probes of the candidate probes in the region for normalization (i.e., the probes with binding sites that are least distanced in the region for normalization) to produce a probe pair; b) eliminating the lowest ranked probe from the probe pair; and c) repeating acts a) and b) until a pre-determined number of candidate probes have been eliminated. After the pre-determined number of candidate probes have been eliminated, the remaining candidate probes may be employed as normalization probes. Further details of exemplary pairwise selection methods that may be employed herein are described in U.S. application Ser. No. 10/996,323, filed on Nov. 23, 2004, which application is incorporated by reference herein in its entirety.

A method of producing an array is provided. These embodiments generally involve: a) selecting a first set of probes for producing data indicating the copy number of a first region of a genome; b) selecting from a candidate set of probes a sub-set of normalization probes that detect a second region, as described above; and c) fabricating an array comprising the first set of probes and the set of normalization probes, to producing the array.

Arrays can be fabricated using any means, including drop deposition from pulse jets or from fluid-filled tips, etc, or using photolithographic means. Either polynucleotide precursor units (such as nucleotide monomers), in the case of in situ fabrication, or previously synthesized polynucleotides (e.g., oligonucleotides, amplified cDNAs or isolated BAC, bacteriophage and plasmid clones, and the like) can be deposited. Such methods are described in detail in, for example U.S. Pat. Nos. 6,242,266, 6,232,072, 6,180,351, 6,171,797, 6,323,043, etc.

Computer-related Embodiments

A variety of computer-related embodiments are also provided. Specifically, a computer-based method for selecting a set of normalization probes for a CGH array using the methods described above; is provided. In one embodiment, the method comprises the following acts: a) inputting a region of a genome for data normalization; and b) executing computer readable instructions for selecting from a larger set of validated probes a sub-set of normalization probes that detect that region. This method may further comprise inputting a desired number of normalization probes. In certain embodiments, the computer readable instructions may be executed locally or remotely to the inputting act.

In many embodiments, the methods are coded onto a computer-readable medium in the form of "programmting", where the term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A computer-based system comprising the above-referenced computer readable medium is also provided. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Arrays

Arrays employed in comparative genome hybridization assays (CGH assays) contain an array of nucleic acid probes immobilized on a substrate, e.g., a solid support. Array platforms for performing array-based comparative genome hybridization methods are known in the art (e.g., see Pinkel et al., Nat. Genet. (1998) 20:207-211; Hodgson et al., Nat. Genet. (2001) 29:459-464; Wilhelm et al., Cancer Res. (2002) 62: 957-960). In certain aspects, CGH arrays contain a plurality (i.e., about 1000 or more, about 2000 or more, about 5000 or more, about 10,000 or more, about 20,000 or more, usually up to about 50,000 100,000 or more) of addressable features each containing a nucleic acid probe that is linked to a substrate, e.g., a planar substrate. Features on an array employed in the subject methods contain nucleic acid probes that hybridize with, i.e., bind to, genome sequences. Accordingly, the arrays used in the subject methods can contain plurality of different cDNAs, oligonucleotides, or inserts from phage or plasmids, etc., that are addressably arrayed. The CGH arrays employed herein may contain surface bound nucleic acid probes that are about 10-200 bases in length, about 201-5000 bases in length, about 5001-50,000 bases in length, or about 50,001-200,000 bases in length, depending on the platform used. In certain embodiments, the subject features contain oligonucleotides that are about 10 to about 200 bases, however, in certain embodiments, the oligonucleotides may be about 10 to about 100 bases, about 10 to about 80 bases, about 10 to about 50 bases, or about 10 to about 30 bases in length. In particular embodiments, the subject features contain oligonucleotides are 20-60 bases in length.

The array produced using the above methods contain a set of probes for a first region of a genome (where the first region is to be analyzed using the array), and a set of normalization probes for a second region of that genome. Depending on the design of the array and how many probes may present on the array, a portion of the probes on the array may be normalization probes, and the remainder of the probes may be probes for the analysis of the first region. In certain embodiments, at least 10%, at least 20%, at least 30%, at least 40%, at least 50%, at least 60%, at least 70%, at least 80%, up to about 90% of the probes on a subject array may be normalization probes and the remaining probes may be analysis probes. In certain embodiments, a subject array may contain about 1000 to about 20,000 normalization probes selected using the methods described above. The normalization probes and the analysis probes may be interspersed with each other, or spatially separate.

At least the normalization probes (i.e., the normalization probes and, in certain embodiments, both the normalization probes and the analysis probes) of a subject array may possess similar thermodynamic properties.

A significant number (e.g., at least 60%, at least 70%, at least 80%, at least 90%, at least 95%, at least 98% or at least 99%) of the at least the normalization probes of a subject array possess a duplex Tm value which falls within a narrow Tm distribution or $\Delta$Tm of about 0.25° C. to about 5° C., e.g., about 0.25° C. to about 3° C., or 0.25° C. to about 2° C. $\Delta$Tm is defined as a temperature distribution in which Tm median is approximately in the center of the distribution. Probes which are within the delta Tm may have a duplex Tm greater than the median Tm−(delta Tm)/2 but, less than median Tm+(delta Tm)/2. Most of the melting temperatures spanned by the delta Tm usually fall within the temperature range of about 65° C. to about 90° C. when calculated by the method described in J Breslauer et al. Proc Natl Acad Sci. (PNAS) 1986 June; 83(11): 3746-3750, where the target and probe concentrations are both 0.1 pM and the salt concentration term is set equal to zero.

A significant number (e.g., at least 60%, at least 70%, at least 80%, at least 90%, at least 95%, at least 98% or at least 99%) of at least the normalization probes have a duplex Tm value ranging from about 65° C. to about 85° C., e.g., from about 75° C. to about 85° C. or from about 78° C. to about 82° C. Tm values for a particular probe may varying due to the salt concentration in the probe solution, target concentration, probe concentration as well as other factors. In one embodiment, the percent of normalization probes on an array which have a duplex Tm value between 65° C. to about 85° C. is in the range of about 90% to about 100%. In another embodiment, the percent of normalization probes on an array which have a duplex Tm value between 75° C. to about 85° C. is about 90% to about 99%.

In certain embodiments, at least the normalization probes have a nucleotide length ranging from about 20 nucleotides to about 100 nucleotides, usually about 40 nucleotides to 70 nucleotides, and more usually about 50 to 65 nucleotides in length. In some embodiments all the probes on the array have the same length, for example a length of about 60 nucleotides. In other embodiments the about 40% to about 60% of all the probes have a length of 60 nucleotides.

In certain embodiments, a significant number (e.g., at least 60%, at least 70%, at least 80%, at least 90%, at least 95%, at least 98% or at least 99%) of at least the normalization probes possess similar GC content, which may, in certain embodiments, fall within a narrow % GC distribution or delta % GC of less than about 10%, e.g., less than about 5%, or less than about 3%. In one embodiment, about 60% to about 99% of the normalization probes have a % GC content from the range of 30% to 40%. In another embodiment, about 60% to about 95% of the normalization probes have a % GC content from the range of 34% to 40%. In yet another embodiment, about 70% to about 90% of the normalization probes have a % GC content from the range of 34% to 40%.

The normalization probes of an array may, in certain embodiments, bind to sequences that are evenly distributed across the second region. In certain embodiments (and dependent on experimental design) no two normalization probes of a subject array bind to genomic sequences that are less than about 100 bp, about 500 bp, about 1 kb, about 5 kb or about 10 kb apart.

Utility

The arrays described above may be employed in array-based CGH binding assays. Such assays may be employed for the quantitative comparison of copy number of one nucleic acid sequence in a first collection of nucleic acid molecules relative to the copy number of the same sequence in a second collection.

A method comprising: contacting an array according to the above with a sample; detecting binding of the sample to the first set of probes to produce data; and normalizing the data using results obtained from the set of normalization probes is provided.

In general, the subject assays involve labeling a test and a reference genomic sample to make two labeled populations of nucleic acids which may be distinguishably labeled, contacting the labeled populations of nucleic acids with an array of surface bound polynucleotides under specific hybridization conditions, and analyzing any data obtained from hybridization of the nucleic acids to the surface bound polynucleotides. Such methods are generally well known in the art (see, e.g., Pinkel et al., Nat. Genet. (1998) 20:207-211; Hodgson et al., Nat. Genet. (2001) 29:459-464; Wilhelm et al., Cancer Res. (2002) 62: 957-960)) and, as such, need not be described herein in any great detail.

Two different genomic samples may be differentially labeled, where the different genomic samples may include an "experimental" sample, i.e., a sample of interest, and a "control" sample to which the experimental sample may be compared. In certain embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell type may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells, or in different phases of the cell cycle) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells.

The genomic sample (containing intact, fragmented or enzymatically amplified chromosomes, or amplified fragments of the same), are distinguishably labeled using methods that are well known in the art (e.g., primer, extension, random-priming, nick translation, etc.; see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). The samples are usually labeled using "distinguishable" labels in that the labels that can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), fluorescein and Texas red (Dupont, Bostan Mass.) and POPRO3 TOPRO3 (Molecular Probes, Eugene, Oreg.). Further suitable distinguishable detectable labels may be found in Kricka et al. (Ann Clin Biochem. 39:114-29, 2002).

The labeling reactions produce a first and second population of labeled nucleic acids that correspond to the test and reference chromosome compositions, respectively. After nucleic acid purification and any optional pre-hybridization steps to suppress repetitive sequences (e.g., hybridization with Cot-1 DNA), the populations of labeled nucleic acids are contacted to an array of surface bound polynucleotides, as discussed above, under conditions such that nucleic acid hybridization to the surface bound polynucleotides can occur, e.g., in a buffer containing 50% formamide, 5×SSC and 1% SDS at 42° C., or in a buffer containing 5×SSC and 1% SDS at 65° C., both with a wash of 0.2×SSC and 0.1% SDS at 65° C.

The labeled nucleic acids can be contacted to the surface bound polynucleotides serially, or, in other embodiments, simultaneously (i.e., the labeled nucleic acids are mixed prior to their contacting with the surface-bound polynucleotides). Depending on how the nucleic acid populations are labeled (e.g., if they are distinguishably or indistinguishably labeled), the populations may be contacted with the same array or different arrays. Where the populations are contacted with different arrays, the different arrays are substantially, if not completely, identical to each other in terms of target feature content and organization.

Standard hybridization techniques (using high stringency hybridization conditions) are used to probe a target nucleic acid array. Suitable methods are described in references describing CGH techniques (Kallioniemi et al., Science 258: 818-821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Gall et al. Meth. Enzymol., 21:470-480 (1981) and Angerer et al. in Genetic Engineering: Principles and Methods Setlow and Hollaender, Eds. Vol 7, pgs 43-65 (plenum Press, New York 1985). See also U.S. Pat. Nos. 6,335,167, 6,197,501; 5,830,645; and 5,665,549; the disclosures of which are herein incorporate by reference.

Generally, comparative genome hybridization methods comprise the following major steps: (1) immobilization of polynucleotides on a solid support; (2) pre-hybridization treatment to increase accessibility of support-bound polynucleotides and to reduce nonspecific binding; (3) hybridization of a mixture of labeled nucleic acids to the surface-bound nucleic acids, typically under high stringency conditions; (4)

post-hybridization washes to remove nucleic acid fragments not bound to the solid support polynucleotides; and (5) detection of the hybridized labeled nucleic acids. The reagents used in each of these steps and their conditions for use vary depending on the particular application.

As indicated above, hybridization is carried out under suitable hybridization conditions, which may vary in stringency as desired. In certain embodiments, highly stringent hybridization conditions may be employed. The term "high stringent hybridization conditions" as used herein refers to conditions that are compatible to produce nucleic acid binding complexes on an array surface between complementary binding members, i.e., between the surface-bound polynucleotides and complementary labeled nucleic acids in a sample. Representative high stringency assay conditions that may be employed in these embodiments are provided above.

The above hybridization step may include agitation of the immobilized polynucleotides and the sample of labeled nucleic acids, where the agitation may be accomplished using any convenient protocol, e.g., shaking, rotating, spinning, and the like.

Following hybridization, the array-surface bound polynucleotides are typically washed to remove unbound labeled nucleic acids. Washing may be performed using any convenient washing protocol, where the washing conditions are typically stringent, as described above.

Following hybridization and washing, as described above, the hybridization of the labeled nucleic acids to the targets is then detected using standard techniques so that the surface of immobilized targets, e.g., the array, is read. Reading of the resultant hybridized array may be accomplished by illuminating the array and reading the location and intensity of resulting fluorescence at each feature of the array to detect any binding complexes on the surface of the array. For example, a scanner may be used for this purpose, which is similar to the AGILENT MICROARRAY SCANNER available from Agilent Technologies, Palo Alto, Calif. Other suitable devices and methods are described in U.S. patent application Ser. No. 09/846,125 "Reading Multi-Featured Arrays" by Dorsel et al.; and U.S. Pat. No. 6,406,849, which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, the subject methods include a step of transmitting data or results from at least one of the detecting and deriving steps, also referred to herein as evaluating, as described above, to a remote location.

Accordingly, a pair of chromosome compositions is labeled to make two populations of labeled nucleic acids, the nucleic acids contacted with an array of surface-bound polynucleotides, and the level of labeled nucleic acids bound to each surface-bound polynucleotide is assessed.

In certain embodiments, a surface-bound polynucleotide is assessed by determining the level of binding of the population of labeled nucleic acids to that polynucleotide. The term "level of binding" means any assessment of binding (e.g. a quantitative or qualitative, relative or absolute assessment) usually done, as is known in the art, by detecting signal (i.e., pixel brightness) from the label associated with the labeled nucleic acids. Since the level of binding of labeled nucleic acid to a surface-bound polynucleotide is proportional to the level of bound label, the level of binding of labeled nucleic acid is usually determined by assessing the amount of label associated with the surface-bound polynucleotide.

In certain embodiments, a surface-bound polynucleotide may be assessed by evaluating its binding to two populations of nucleic acids that are distinguishably labeled. In these embodiments, for a single surface-bound polynucleotide of interest, the results obtained from hybridization with a first population of labeled nucleic acids may be compared to results obtained from hybridization with the second population of nucleic acids, usually after normalization of the data. The results may be expressed using any convenient means, e.g., as a number or numerical ratio, etc.

As discussed above, results obtained from the normalization probes may be employed to normalize the data obtained from the analysis probes. Several normalization strategies have been described (Quackenbush et al, Nat Genet. 32 Suppl:496-501, 2002, Bilban et al Curr Issues Mol Biol. 4:57-64, 2002, Finkelstein et al, Plant Mol Biol. 48(1-2):119-31, 2002, and Hegde et al, Biotechniques. 29:548-554, 2000). Specific examples of normalization suitable for use in the subject methods include linear normalization methods, non-linear normalization methods, e.g., using lowess local regression to paired data as a function of signal intensity, signal-dependent non-linear normalization, qspline normalization and spatial normalization, as described in Workman et al., (Genome Biol. 2002 3, 1-16). In certain embodiments, the numerical value associated with a feature signal is converted into a log number, either before or after normalization occurs. Further exemplary normalization methods that employ normalization probes are described in: U.S. patent application Ser. No. 10/825,893, filed on Apr. 16, 2004 and published as 20050234650; U.S. patent application Ser. No. 11/086,253, filed on Mar. 22, 2005 and published as 20050221357, U.S. patent application Ser. No. 10/686,092 filed on Oct. 14, 2003 and published as 20050079509; and U.S. patent application Ser. No. 10/140,575 filed on May 7, 2002 and published as 20030216870, which are incorporated by reference herein.

Using results produced using the instant normalization probes, dye-normalized expression ratios may be computed by feature extraction software. For example, many feature extraction systems use algorithms for filter and smoothing, such as LOESS, or LOWESS, for example to standardize the normalization line based on the normalization probes and to computer expression ratio readings for other probes that are differentially expressed. For example, such systems, for each array, take the normalization probes which are closest to the diagonal and normalize them to fit to the diagonal/curve that indicates no differential expression; then calculate log ratios of differentially expressed probes relative to the normalization curve.

Accordingly, binding of a surface-bound polynucleotide to a labeled population of nucleic acids may be assessed. In certain embodiments, the assessment provides a numerical assessment of binding, and that numeral may correspond to an absolute level of binding, a relative level of binding, or a qualitative (e.g., presence or absence) or a quantitative level of binding. Accordingly, a binding assessment may be expressed as a ratio, whole number, or any fraction thereof.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of selecting a set of normalization probes for use on a comparative genome hybridization array, comprising:
   a) selecting a first region of a genome to be evaluated by comparative genome hybridization to produce data;
   b) selecting a second region of said genome for normalization of said data, and
   c) selecting from a set of candidate probes a sub-set of normalization probes that detect said second region using a computer, wherein candidate probes are ranked and wherein said sub-set of normalization probes are selected using an iterative pairwise elimination method that comprises pairing the probes of said candidate probes that are most proximal to one another to produce a probe pair; eliminating the lowest ranked probe from the probe pair; and repeating said pairing and eliminating steps until a pre-determined number of candidate probes have been eliminated to select said set of normalization probes.

2. The method of claim 1, wherein said normalization probes are distributed across said second region.

3. The method of claim 1, wherein said first region of said genome is distinct from said second region of said genome.

4. The method of claim 1, wherein said second region of said genome includes said first region of said genome.

5. The method of claim 1, wherein said second region is an entire genome, excluding said first region of said genome.

6. The method of claim 1, wherein said second region of said genome is expected to have a known copy number.

7. The method of claim 1, wherein the probes of said set of candidate probes are ranked according to at least one property.

8. The method of claim 1, wherein said first region of said genome ranges in length from 10 kb to the length of an entire chromosome.

9. The method of claim 1, wherein said set of normalization probes comprises 1,000 or more normalization probes.

10. The method of claim 1, wherein said normalization probes are oligonucleotide probes.

11. A method of producing an array, comprising:
    a) selecting a first set of probes for producing data indicating the copy number of a first region of a genome;
    b) selecting a second region of said genome for normalization of said data,
    c) selecting from a set of candidate probes a sub-set of normalization probes that detect said second region, wherein said candidate probes are ranked and wherein said sub-set of normalization probes are selected using an iterative pairwise elimination method that comprises pairing the probes of said candidate probes that are most proximal to one another to produce a probe pair; eliminating the lowest ranked probe from the probe pair; and repeating said pairing and eliminating steps until a pre-determined number of candidate probes have been eliminated; and
    d) fabricating an array comprising said first set of probes and said set of normalization probes;
    to produce said array.

12. The method of claim 11, wherein said first region of said genome is distinct from said second region of said genome.

13. The method of claim 11, wherein said second region encompasses said first region.

14. The method of claim 11, wherein said probes are oligonucleotide probes.

15. A method comprising:
    contacting said array produced according to the method of claim 11 with a sample;
    detecting binding of said sample to said first set of probes to produce data; and;
    normalizing said data using results obtained from said set of normalization probes.

16. An array made by:
    a) selecting a first set of probes for producing data indicating the copy number of a first region of a genome;
    b) selecting a second region of said genome for normalization of said data,
    c) selecting from a set of candidate probes a sub-set of normalization probes that detect said second region, wherein said candidate probes are ranked and wherein said sub-set of normalization probes are selected using an iterative pairwise elimination method that comprises pairing the probes of said candidate probes that are most proximal to one another to produce a probe pair; eliminating the lowest ranked probe from the probe pair; and repeating said pairing and eliminating steps until a pre-determined number of candidate probes have been eliminated; and
    d) fabricating an array comprising said first set of probes and said set of normalization probes.

17. The array of claim 16, wherein said array comprises:
    a) a first set of probes for producing data indicating the copy number of a first region of a genome; and
    b) a set of normalization probes that bind to a second region of said genome.

18. The array of claim 17, wherein said first region of said genome is distinct from said second region of said genome.

19. The array of claim 17, wherein said second region of said genome includes said first region of said genome.

20. The array of claim 16, wherein said probes are oligonucleotide probes.

21. A computer-based method for selecting a set of normalization probes for a comparative genome hybridization (CGH) array, comprising the following acts:
    inputting a region of a genome for data normalization into a computer; and,
    executing computer readable instructions on said computer for selecting from a set of candidate probes a sub-set of normalization probes that detect a second region, wherein said candidate probes are ranked and wherein said sub-set of normalization probes are selected using an iterative pairwise elimination method that comprises pairing the probes of said candidate probes that are most proximal to one another to produce a probe pair; eliminating the lowest ranked probe from the probe pair; and repeating said pairing and eliminating steps until a pre-determined number of candidate probes have been eliminated;

to select said set of normalization probes for said CGH array.

22. The computer-based method of claim 21, further comprising inputting a desired number of normalization probes.

23. The computer-based method of claim 21, wherein said executing act is done locally to said inputting act.

24. The computer-based method of claim 21, wherein said executing act is done, at a remote location to said inputting act.

25. A physical computer-readable medium comprising:
programming for performing the following method:
inputting a region of a genome for data normalization; and,
executing computer readable instructions for selecting from a set of candidate probes a sub-set of normalization probes that detect a second region, wherein said candidate probes are ranked and wherein said sub-set of normalization probes are selected using an iterative pairwise elimination method that comprises pairing the probes of said candidate probes that are most proximal to one another to produce a probe pair; eliminating the lowest ranked probe from the probe pair; and repeating said pairing and eliminating steps until a pre-determined number of candidate probes have been eliminated;

to select said set of normalization probes for said CGH array.

26. A computer-system comprising:
the computer-readable medium of claim 25.

* * * * *

UNITED STATES PATENT AND TRADEMARK OFFICE
CERTIFICATE OF CORRECTION

PATENT NO. : 8,221,978 B2
APPLICATION NO. : 12/279570
DATED : July 17, 2012
INVENTOR(S) : Jing Gao et al.

Page 1 of 1

It is certified that error appears in the above-identified patent and that said Letters Patent is hereby corrected as shown below:

In column 23, line 14, in Claim 24, delete "done," and insert -- done --, therefor.

Signed and Sealed this
Twenty-eighth Day of August, 2012

David J. Kappos
*Director of the United States Patent and Trademark Office*